US00PP31859P2

(12) United States Plant Patent
Egger

(10) Patent No.: US PP31,859 P2
(45) Date of Patent: Jun. 9, 2020

(54) ***HEUCHERA* PLANT NAMED 'SHIMMER'**

(50) Latin Name: ***Heuchera* hybrid**
Varietal Denomination: Shimmer

(71) Applicant: Terra Nova Nurseries, Inc., Canby, OR (US)

(72) Inventor: Janet N. Egger, Seattle, WA (US)

(73) Assignee: Terra Nova Nurseries, Inc, Canby, OR (US)

( * ) Notice: Subject to any disclaimer, the term of this patent is extended or adjusted under 35 U.S.C. 154(b) by 0 days.

(21) Appl. No.: 16/501,777

(22) Filed: Jun. 4, 2019

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 6/80
See application file for complete search history.

(56) References Cited

PUBLICATIONS

Trademark hit on 'Shimmer' (Cancelled), serial No. 77108980, filing date Feb. 16, 2007.*

* cited by examiner

*Primary Examiner* — Anne Marie Grunberg
(74) *Attorney, Agent, or Firm* — Klarquist Sparkman, LLP

(57) ABSTRACT

A new and distinct *Heuchera* plant characterized by small, strong veiled, blue green leaves, short flowering stems, pink flowers, a small, mounding habit with excellent crown count, and excellent vigor.

1 Drawing Sheet

Botanical denomination: *Heuchera* hybrid.
Variety designation: 'Shimmer'.
Trademark designation: LITTLE CUTIES™ 'Shimmer'

BACKGROUND OF THE INVENTION le;.4qThe present invention relates to a new and distinct cultivar of *Heuchera* given the cultivar name of 'Shimmer'. *Heuchera* is in the family Saxifragaceae. *Heuchera* 'Shimmer' was bred to be a miniature *Heuchera* for small pots that is ever-blooming. *Heuchera* 'Shimmer' originated as a controlled cross using *Heuchera* 'B360-2', a proprietary, unpatented, unnamed plant as the seed parent, and *Heuchera* 'B369-1', a proprietary, unpatented, unnamed plant as the pollen parent.

Compared to the seed parent, *Heuchera* 'B360-2', the new cultivar has leaves that are green rather than black, darker pink flowers, a stronger veil.

Compared to the pollen parent, *Heuchera* 'B369-1', the new cultivar has green leaves rather than purple leaves, pink flowers rather than purple and white, a stronger veil, and a denser crown.

Compared to *Heuchera* 'Peppermint', U.S. Plant Pat. No. 24,563, the new cultivar has a stronger veil.

This new *Heuchera* is uniquely distinguished by:

1. small, strong veiled, blue green leaves,
2. short flowering stems,
3. pink flowers,
4. small, mounding habit with excellent crown count, and
5. excellent vigor.

This new cultivar has been reproduced only by asexual propagation (tip cuttings and tissue culture using growing tips). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

FIG. 1 shows a twelve-month-old plant of *Heuchera* 'Shimmer' growing in a six-inch pot in a greenhouse in early December in Canby, Oreg.

DETAILED PLANT DESCRIPTION

The following is a detailed description of the new *Heuchera* cultivar based on observations taken in October of nine-month-old specimens growing in six-inch pots in a warm greenhouse in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* $5^{th}$ edition, 2007.

Plant:

*Form.*—Basal rosette, herbaceous perennial.
*Hardiness.*—USDA Zone 4 to 9.
*Size.*—12.5 cm tall from soil to foliage, 28 cm wide.
*Number of crowns.*—About 7.
*Habit.*—Small, mounding.
*Vigor.*—Excellent.

Leaf:
*Type*.—Simple.
*Arrangement*.—Rosette.
*Shape*.—Broadly ovate.
*Number*.—About 65.
*Blade size*.—Grows to 8.5 cm long and 8 cm wide.
*Venation*.—Palmate.
*Lobing/division*.—4 main lobes palmate lobes.
*Margins*.—Crenate, undulate.
*Apex*.—Mucronulate.
*Base*.—Cordate, strongly overlapping and often spiraling in.
*Surface texture*.—Glandular-puberulent on both sides.
*Leaf rugosity*.—Medium.
*Leaf undulation*.—Weak.
*Petiole description*.—Grows to 8 cm long and 3 mm wide, glandular hairs.
*Leaf color*.—Top side closest to Greyed Green 189C with veins Green 136A, bottom side Greyed Green 191B with veins Greyed Green 191B.
*Glossiness*.—Weak.

Inflorescence:
*Size*.—Grows to 10.5 cm long and 5.5 cm wide.
*Type*.—Thyrse, strong, upright.
*Number of thyrse*.—About 13.
*Number of flowers per thyrse*.—About 50.
*Peduncle*.—Grows to 12 cm long and 2.5 mm wide at base, glandular hairs.
*Flowering stem attitude*.—Upwards.
*Pedicel*.—Variable in size, with glandular hairs, Brown 200C.
*Bloom period*.—April through late October in Canby, Oreg.

Flower bud:
*Size*.—5 mm long and 2.5 mm long.
*Description*.—Glandular puberulent, ovoid, down facing.
*Color*.—Red Purple N66C.

Flower:
*Type*.—Perfect.
*Shape*.—Campanulate.
*Attitude*.—Down and side-facing.
*Density*.—Medium.
*Size*.—6.5 mm long and 5 mm wide.
*Corolla description*.—5 petals, each 2.0 mm long and 0.5 mm wide, spatulate, margins entire, tip acute, glandular-puberulent on bottom side, glabrous on top side, both sides Red Purple 73D.
*Calyx description*.—Campanulate, 4.5 mm long and 6 mm wide, with 5 lobes with narrow sinuses divided ½ way to the base, each 2 mm wide and 2.5 mm long, oblong in shape, both sides glandular-puberulent with glandular hairs (Red Purple 61C), tip obtuse, margin entire, both sides between Red Purple 58C and Red Purple 58D, strongest at base.
*Stamen description*.—5 in number, filaments 1.5 mm long, White NN155C, anthers 0.5 mm long, Greyed Orange 165A, pollen Greyed Orange 167A.
*Pistil description*.—1, 2-beaked, 6 mm long and 0.5 mm wide, White 155D overall, ovary 2 mm long and 2 mm wide, style 4 mm long.
*Lastingness*.—Each thyrse blooms for about 3 weeks on the plant.

Fruit and seed:
*Type*.—Two-beaked ovoid capsule.
*Size*.—4 mm long and 3 mm wide.
*Fertility*.—Low.
*Color*.—Greyed Brown 199C.

Seed:
*Shape*.—Linear.
*Size*.—2 mm long.
*Color*.—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

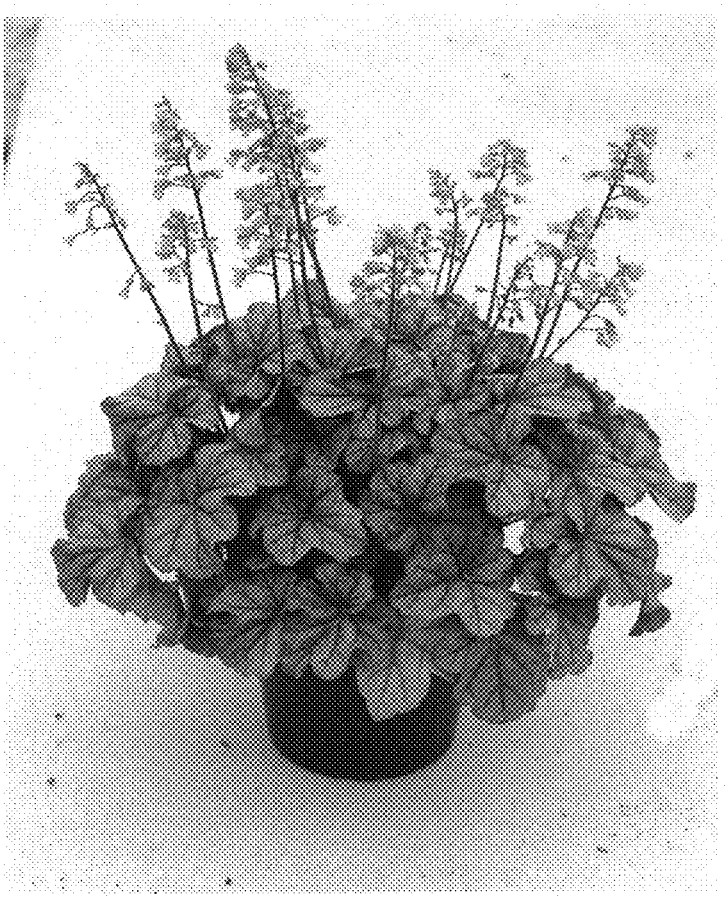

* * * * *